US006486210B2

(12) United States Patent
Reddy et al.

(10) Patent No.: US 6,486,210 B2
(45) Date of Patent: Nov. 26, 2002

(54) SUBSTITUTED STYRYL BENZYLSULFONES FOR TREATING PROLIFERATIVE DISORDERS

(75) Inventors: E. Premkumar Reddy, Villanova, PA (US); M. V. Ramana Reddy, Upper Darby, PA (US)

(73) Assignee: Temple University—Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/833,287

(22) Filed: Apr. 12, 2001

(65) Prior Publication Data

US 2002/0115643 A1 Aug. 22, 2002

Related U.S. Application Data

(60) Provisional application No. 60/197,849, filed on Apr. 14, 2000, provisional application No. 60/234,707, filed on Sep. 22, 2000, and provisional application No. 60/271,640, filed on Feb. 27, 2001.

(51) Int. Cl.[7] .............................................. A61K 31/10
(52) U.S. Cl. ........................................ 514/708; 568/28
(58) Field of Search ............................. 568/28; 514/708

(56) References Cited

U.S. PATENT DOCUMENTS

| 2,532,612 | A | 12/1950 | Doumani | 260/609 |
|---|---|---|---|---|
| 3,185,743 | A | 5/1965 | Combe et al. | 260/682 |
| 3,418,101 | A | 12/1968 | Buchholtz et al. | 71/72 |
| 3,514,386 | A | 5/1970 | Oswald et al. | 204/162 |
| 3,917,714 | A | 11/1975 | Richmond | 260/607 A |
| 4,161,407 | A | 7/1979 | Campbell | 96/114 |
| 4,386,221 | A | 5/1983 | Hyatt et al. | 568/28 |
| 4,937,388 | A | 6/1990 | Bushell et al. | 568/56 |
| 5,659,087 | A | 8/1997 | Aikins et al. | 568/27 |
| 6,201,154 | B1 * | 3/2001 | Reddy et al. | 568/28 |

FOREIGN PATENT DOCUMENTS

WO    WO99/18068    4/1999

OTHER PUBLICATIONS

CA:110:74956 abs of Org Prep Proced Int by D Reddy et al 10(3) pp 205–12 1988.*
CA:115:158544 abs of Sulfur Lett by D Reddy et al 13(2) pp 83–90 1991.*
CA:132:263142 abs of Pathol Biol by Hillaire et al 47(9) pp 895–902.*
CA:130:336836 abs of Med Hypotheses by Olson 51(6) pp 493–498 1998.*
D. Bhaskar Reddy, N.S. Reddy, S. Reddy, M.V.R. Reddy and S. Balasubramanyam, *Org. Prep. Proc. Int.*, 20(3):205–212 (1988).
D. Bhasker Reddy, P. V. Ramana Reddy, V. Padmavathi, and M.V.R. Reddy, *Sulfur Lett.*, 13(2):83–90 (1991).

(List continued on next page.)

Primary Examiner—Jean F. Vollano
(74) Attorney, Agent, or Firm—Drinker Biddle & Reath LLP

(57) ABSTRACT

Styryl benzylsulfones of formula I are useful as antiproliferative agents, including, for example, anticancer agents:

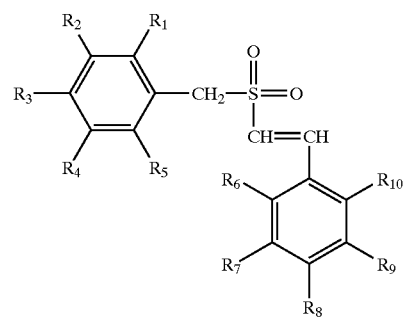

wherein (a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or (b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl;

or a pharmaceutically acceptable salt thereof.

86 Claims, No Drawings

OTHER PUBLICATIONS

M.V.R. Reddy and S. Reddy, *Acta Chim. Acad. Sci. Hung.*, 115(3):269–271 (1984).

M.V.R. Reddy, V. Vijayalakshmi, D. Bhaskar Reddy and P.V. Ramana Reddy, *Phosphorus, Sulfur Silicon Relat. Elem.*, 60:209–214 (1991).

M.V. Reddy and S. Reddy, *Acta Chim. Acad. Sci. Hung.*, 120(4):275–280 (1985).

M.V.R. Reddy and S. Reddy, *Synthesis* No. 4, 322–323 (1984).

M.V.R. Reddy, S. Reddy and D.B. Reddy, *Sulfur Lett.*, 7(2):43–48 (1987).

Reddy et al., "A New Route for the Synthesis of Styrylbenzylsulfones, Precursors of 1–Benzylsulfonyl–2–Arylcyclopropanes", *Phosphorus, Sulfur, and Silicon*, 53:285–290 (1990).

Mieczyslaw Makosza and Irina Krylova, "Some Reactions of the Chloromethyl trans–beta– Styryl Sulfone Carbanion", *Liebigs Ann./Recueil*, pp. 2337–2340 (1997).

Reddy et al., "Phase Transfer Catalysis—A Facile Method for Cyclopropanation of Some Isomeric Styryl Benzyl Sulfones and BIS (Styryl) Sulfones", *Acta Chim. Hung.*, 131(1):83–92 (1994).

CA:124:175763, abs of Reddy et al., *Indian J. Heterocycl. Chem.*, (May 1995), 5(1), 11–14.

CA:124:146025, abs of Reddy et al., *Indian J. Heterocycl. Chem.* (1995), 4(4), 259–264.

CA:126:166162, Thompson et al. abs of *Cancer Res.*, (Feb. 1997) 57(2), 267–271.

Benati, et al., *J. Org. Chem.*, 59:2818–2823 (1994).

CA:120:323356 abs of Reddy et al., *Sulf. Lett.* (1993), 16(5–6), 227–35.

CA:122:132682 abs of Reddy et al., *Phosphorus, Sulfur Silicon Relat. Elem.* (1994), 90(1–4), 1–10.

CA:124:8731 abs of Reddy et al., *Indian J. Chem. Sect. B: Org. Chem. Incl. Med. Chem.* (1995) 34B(9), 816–22.

CA:76:121420 abs of Findlay et al. *Brit J. Dermatol.*, Suppl. (1971), No. 7, 44–9.

CA:105:133446 abs of Naidu et al., *Proc.—Indian Acad. Sci., Chem. Sci* (1985), 95(4), 391–5.

CA:126:185889 abs of Japanese Pat. App. 09–03,037 (Jan. 7, 1997).

U.S. Pat. App. Ser. No. 09/689,281 filed Oct. 11, 2000, of Stephen C. Cosenza, M.V. Ramana Reddy and E. Premkumar Reddy.

* cited by examiner

SUBSTITUTED STYRYL BENZYLSULFONES FOR TREATING PROLIFERATIVE DISORDERS

CROSS-REFERENCE TO RELATED APPLICATIONS

The benefit of the filing dates of the following provisional applications is claimed pursuant to 35 U.S.C. 119(e): Ser. No. 60/197,849, filed Apr. 14, 2000; Ser. No. 60/234,707, filed Sep. 22, 2000; and Ser. No. 60/271,640, filed Feb. 27, 2001. The entire disclosures of the aforementioned provisional applications are incorporated herein by reference.

FIELD OF THE INVENTION

The invention relates to compositions and methods for the treatment of cancer and other proliferative disorders.

BACKGROUND OF THE INVENTION

Extracellular signals received at transmembrane receptors are relayed into the cells by the signal transduction pathways (Pelech et al., *Science* 257:1335 (1992)) which have been implicated in a wide array of physiological processes such as induction of cell proliferation, differentiation or apoptosis (Davis et al., *J. Biol. Chem.* 268:14553 (1993)). The Mitogen Activated Protein Kinase (MAPK) cascade is a major signaling system by which cells transduce extracellular cues into intracellular responses (Nishida et al., *Trends Biochem. Sci.* 18:128 (1993); Blumer et al., *Trends Biochem. Sci.* 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., *Science* 255:212 (1992); Biggs III et al., *Proc. Natl. Acad. Sci. USA* 89:6295 (1992); Garner et al., *Genes Dev.* 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., *Genes Dev.* 7:2135 (1993)). JNKs are members of the class of stress-activated protein kinases (SPKs). JNKs have been shown to be activated by treatment of cells with UV radiation, pro-inflammatory cytokines and environmental stress (Derijard et al., *Cell* 1025 (1994)). The activated JNK binds to the amino terminus of the c-Jun protein and increases the protein's transcriptional activity by phosphorylating it at ser63 and ser73 (Adler et al., *Proc. Natl. Acad. Sci. USA* 89:5341 (1992); Kwok et al., *Nature* 370:223 (1994)).

Analysis of the deduced primary sequence of the JNKs indicates that they are distantly related to ERKs (Davis, *Trends Biochem. Sci.* 19:470 (1994)). Both ERKs and JNKs are phosphorylated on Tyr and Thr in response to external stimuli resulting in their activation (Davis, *Trends Biochem. Sci.* 19:470 (1994)). The phosphorylation (Thr and Tyr) sites, which play a critical role in their activation are conserved between ERKs and JNKs (Davis, *Trends Biochem. Sci.* 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., *Nature* 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., *Annu Rev Biochem* 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., *Eur. J. Biochem.* 135:583–589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What is also needed are new cell antiproliferative agents, and anticancer therapeutics in particular, which are highly selective in the killing of proliferating cells such as tumor cells, but not normal cells.

SUMMARY OF THE INVENTION

It is an object of the invention to provide compounds, compositions and methods for the treatment of cancer and other proliferative diseases. The biologically active compounds are in the form of styryl benzylsulfones.

It is an object of the invention to provide compounds which are selective in killing tumor cells but not normal cells.

According to one embodiment of the invention, novel compounds are provided according to formula I:

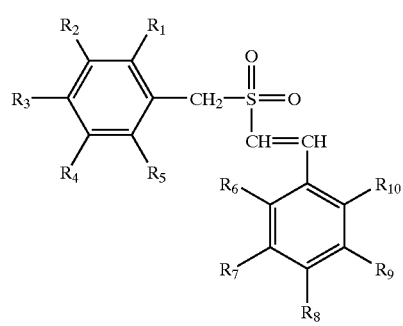

wherein
(a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or (b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl;

or a pharmaceutically acceptable salt thereof.

The styryl benzylsulfones are characterized by cis-trans isomerism resulting from the presence of a double bond. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p. 127–138. Steric relations around a double bond are designated as "Z" or "E". Both configurations are included in the scope of the present invention.

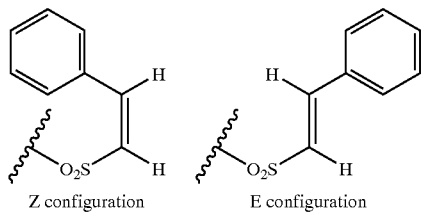

Z configuration    E configuration

According to one embodiment, the benzyl nucleus, that is, the ring system containing $R_1$I through $R_5$, is at least trisubstituted. Thus, in formula I, (i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

According to a preferred sub-embodiment of the aforesaid E-configuration compounds, the benzyl nucleus is penta-substituted with halogen, that is, $R_1$, $R_2$, $R_3$, $R_4$ and $R_5$ are halogen, same or different, and $R_6$, $R_7$, $R_8$, $R_9$ and $R_{10}$ are independently selected from the group consisting of hydrogen, halogen, C1–C6 alkyl and C1–C6 alkoxy. In some embodiments, $R_8$ is halogen or C1–C6 alkoxy.

According to another preferred sub-embodiment of the aforesaid E-configuration compounds, $R_3$ is C1–C6 alkoxy, at least two of $R_1$, $R_2$, $R_4$ and $R_5$ are C1–C6 alkoxy, and the remainder of $R_1$, $R_2$, $R_4$ and $R_5$ are hydrogen.

According to another embodiment, the styryl nucleus, that is, the ring system containing $R_6$ through $R_{10}$, is at least trisubstituted. Thus, in formula I, (i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl.

According to a preferred sub-embodiment, the compounds have the E-configuration and the styryl nucleus is penta-substituted with halogen, that is, $R_6$, $R_7$, $R_8$, $R_9$ and $R_{10}$ are halogen, same or different. $R_1$, $R_2$, $R_3$, $R_4$ and $R_5$ are independently selected from the group consisting of hydrogen, halogen, C1–C6 alkyl and C1–C6 alkoxy. In some such embodiments, $R_3$ is halogen or C1–C6 alkoxy.

According to another embodiment, a compound has the E-configuration and is mono-substituted at the 4-position on the benzyl nucleus. $R_3$ is selected from the group consisting of halogen, C1–C6 alkyl, C1–C6 alkoxy, nitro, cyano, hydroxyl, phosphonato, amino, sulfamyl, acetoxy, dimethylamino(C2–C6 alkoxy) and trifluoromethyl; and $R_1$, $R_2$, $R_4$ and $R_5$ are hydrogen. At least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl. In some embodiments, $R_3$ is halogen and $R_6$, $R_7$, $R_8$, $R_9$ and $R_{10}$ are preferably selected from hydrogen, halogen and C1–C6 alkoxy, provided that at least three of $R_6$, $R_7$, $R_8$, $R_9$ and $R_{10}$ are halogen, C1–C6 alkoxy, or combination thereof.

In a preferred sub-embodiment of 4-position substitution on the benzyl nucleus, the compounds have the formula IV:

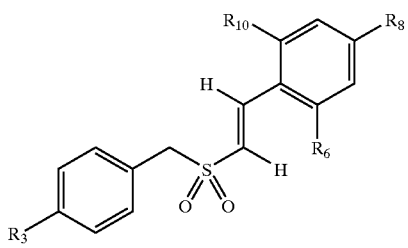

IV wherein $R_3$ and $R_8$ are independently selected from the group consisting of halogen, C1–C6 alkoxy, nitro, cyano, hydroxyl, phosphonato, amino, sulfamyl, acetoxy, dimethylamino(C2–C6 alkoxy) and trifluoromethyl. $R_6$ and $R_{10}$ are independently selected from the group consisting of C1–C6 alkoxy, hydroxyl, phosphonato, amino, sulfamyl, acetoxy, dimethylamino(C2–C6 alkoxy); or a pharmaceutically acceptable salt thereof. In some embodiments, $R_3$ and $R_8$ are independently selected from the group consisting of halogen and C1–C6 alkoxy. $R_6$ and $R_{10}$ are preferably C1–C6 alkoxy, more preferably C1–C3 alkoxy. In some embodiments, $R_3$, $R_6$, $R_8$, and $R_{10}$ are C1–C6 alkoxy, preferably C1–C3 alkoxy. The various alkoxy groups may be the same or different.

According to another embodiment, the compound has the Z-configuration, and the benzyl nucleus, that is, the ring system containing $R_1$ through $R_5$, is at least trisubstituted. Thus, in formula I, (i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

In some such embodiments of Z configuration compound, the benzyl nucleus is trisubstituted with C1–C6 alkoxy, that is, two of $R_1$, $R_2$, $R_3$, $R_4$ and $R_5$ are hydrogen and three of $R_1$, $R_2$, $R_3$, $R_4$ and $R_5$ are C1–C6 alkoxy, preferably, methoxy. In such compounds, the styryl nucleus is unsubstituted, or from mono-substituted up to penta-substituted, particularly penta-substitution with halogen.

According to another embodiment, the compound has the Z configuration and the styryl nucleus, that is, the ring system containing $R_6$ through $R_{10}$, is at least trisubstituted. Thus, in formula I, (i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl.

According to one such embodiment of Z configuration compound, the styryl nucleus is penta-substituted with halogen. $R_6$, $R_7$, $R_8$, $R_9$ and $R_{10}$ are halogen, same or different, but preferably fluorine. In some such embodiments where the styryl nucleus is penta-substituted, $R_1$, $R_2$, $R_3$, $R_4$ and $R_5$ are independently selected from the group consisting of hydrogen, halogen C1–C6 alkyl and C1–C6 alkoxy. In some such embodiments, the benzyl nucleus is trisubstituted with C1–C6 alkoxy, that is, two of $R_1$, $R_2$, $R_3$, $R_4$ and $R_5$ are hydrogen and three of $R_1$, $R_2$, $R_3$, $R_4$ and $R_5$ are C1–C6 alkoxy, preferably methoxy. In other such embodiments, the benzyl nucleus is mono-substituted at the 4-position, that is, $R_1$, $R_2$, $R_4$ and $R_5$ are hydrogen, and $R_3$ is other than hydrogen. In some such mono-substitution sub-embodiments, $R_3$ is C1–C6 alkoxy, preferably methoxy, or halogen.

According to other embodiments of Z configuration compound, the benzyl nucleus is monosubstituted with halogen, particularly at the 4-position, and the styryl nucleus is at least trisubstituted, preferably with halogen.

According to one embodiment of Z configuration compound, $R_1$, $R_2$, $R_3$, $R_4$ and $R_5$ are halogen, same or different, and $R_6$, $R_7$, $R_8$, $R_9$ and $R_{10}$ are independently selected from the group consisting of hydrogen, halogen, C1–C3 alkyl and C1–C3 alkoxy.

According to other embodiments, processes for preparing compounds according to formula I are provided. In one such embodiment, the compound has the E configuration. The compound is prepared by condensing a compound of formula III

III $$R_2 \quad R_1$$
$$R_3-\text{Ar}-CH_2-\overset{O}{\underset{\parallel}{S}}=O$$
$$\underset{R_4 \quad R_5}{} \quad \underset{\parallel}{CH_2COH}$$
$$O$$

with a compound of formula VI:

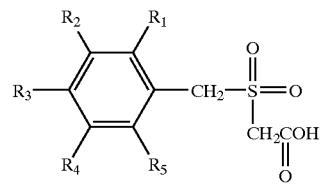

VI wherein (a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or (b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

The formula III compound may be prepared, for example, by reacting sodium glycollate with a benzyl chloride compound of the formula:

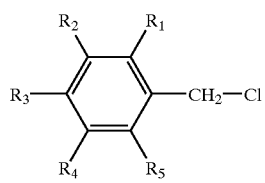

to form a benzylthioacetic acid compound of the formula:

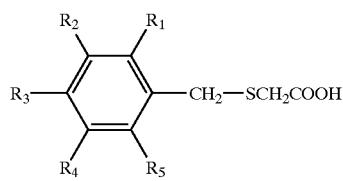

which is then oxidized to form a compound of formula III, wherein $R_1$ through $R_5$ are defined as above.

Alternatively, the benzylthioacetic acid intermediate is prepared by reacting a compound of the formula $HSCH_2COOR$ where R is C1–C6 alkyl with the aforementioned benzyl chloride compound to form a compound of formula II:

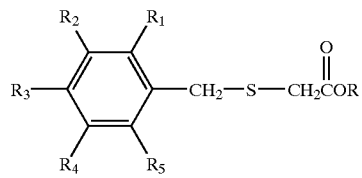

wherein R is C1–C6 alkyl, which is then converted to the corresponding benzylthioacetic acid compound by alkaline or acid hydrolysis.

A process for preparing compounds according to formula I having the Z configuration is provided. A sodium benzylthiolate of the formula:

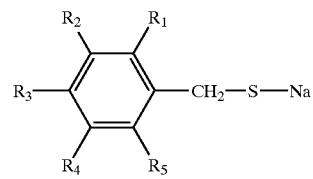

is reacted with a phenylacetylene of the formula:

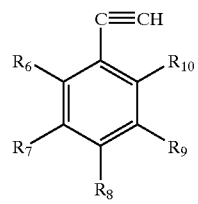

to form a Z-styryl benzylsulfide of formula Ia:

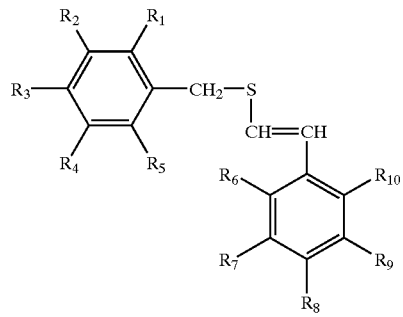

wherein $R_1$ through $R_{10}$ are defined as above. The Z-styryl benzylsulfide is then oxidized to form a compound according to formula I having the Z-configuration The term "alkyl", by itself or as part of another substituent means, unless otherwise stated, a straight or branched chain hydrocarbon radical, including di- and multi-radicals, having the number of carbon atoms designated (i.e. C1–C6 means one to six carbons) and includes straight or branched chain groups. Most preferred is C1–C3 alkyl, particularly ethyl and methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are C1–C3 alkoxy, particularly ethoxy and methoxy.

By "dimethylamino(C2–C6 alkoxy)" is meant $(CH_3)_2N(CH_2)_nO$— wherein n is from 2 to 6. Preferably, n is 2 or 3. Most preferably, n is 2, that is, the group is the dimethylaminoethoxy group: $(CH_3)_2NCH_2CH_2O$—.

By "halogen" is meant fluorine, chlorine, bromine or iodine.

By "phosphonato" is meant the group $—PO(OH)_2$.

By "sulfamyl" is meant the group $—SO_2NH_2$.

Where a substituent on the benzyl or styryl nucleus is an alkyl or alkoxy group, the carbon chain may be branched or straight, with straight being preferred. Preferably, the alkyl and alkoxy groups comprise C1–C3 alkyl and C1–C3 alkoxy, most preferably methyl and methoxy.

By "substituted" means that an atom or group of atoms has replaced hydrogen as the substituent attached to another group.

By "subject" is meant an animal or a human being.

A pharmaceutical composition is also provided comprising a pharmaceutically acceptable carrier and one or more compounds of formula I above, or a pharmaceutically acceptable salt of such compound.

According to another embodiment of the invention, a method of treating an individual for a proliferative disorder, particularly cancer, is provided, comprising administering to said individual an effective amount of a compound according to formula I, or a pharmaceutically acceptable salt of such compound, alone or in combination with a pharmaceutically acceptable carrier.

In another embodiment of the invention, a method of inhibiting growth of tumor cells in an individual afflicted with cancer is provided comprising administering to said individual an effective amount of a compound according to formula I, or a pharmaceutically acceptable salt of such compound, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of a compound according to formula I, or a pharmaceutically acceptable salt of such compound, alone or in combination with a pharmaceutically acceptable carrier.

In another embodiment, novel compounds are provided which are useful as intermediates in preparing the compounds of formula I. The intermediates comprise the compounds of formulae II and III:

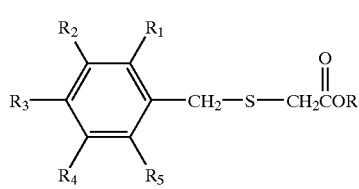

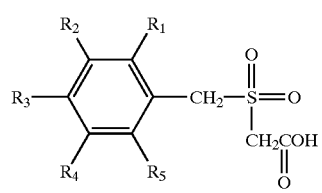

wherein R is hydrogen or C1–C6 alkyl; and at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

According to another embodiment, novel intermediates useful in preparing the compounds of formula I comprise the compounds of formula V

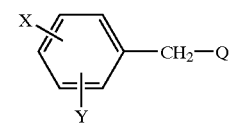

wherein:

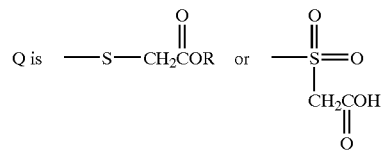

R is H or C1–C6 alkyl; and

X and are Y independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl;

provided: when Y is hydrogen, X may not be hydrogen, 4-chloro, 4-bromo, 4-fluoro or 4-alkoxy.

In one embodiment, X and Y are as defined as above, with the further provision that when Y is hydrogen, X may not be 4-trifluoromethyl, 4-nitro or 4-cyano; and when X is 4-chloro, Y may not be 2-chloro or 3-chloro.

According to a preferred embodiment, intermediates are provided according to formula V wherein Y is hydrogen and X is selected from the group consisting of 4-hydroxy, 4-amino and 4-sulfamyl.

DETAILED DESCRIPTION OF THE INVENTION

According to the present invention, certain highly substituted styryl benzylsulfone derivatives and pharmaceutically acceptable salts thereof selectively kill various tumor cell types without killing normal cells.

At least one of the benzyl or styryl aromatic nuclei is at least tri-substituted. By "substituted" in this context means that an atom or group of atoms has replaced hydrogen as the substituent attached to an aromatic ring carbon atom.

According to certain embodiments, the benzyl and/or styryl aromatic nuclei are tri-substituted, that is, only two of $R_1$ through $R_5$ are hydrogen, and/or only two of $R_6$ through $R_{10}$ are hydrogen. Representative combinations of substituents are set forth in Table 1:

TABLE 1

Tri-Substitution

| | | | |
|---|---|---|---|
| a | Halogen | halogen | Halogen |
| b | Halogen | halogen | C1–C6 alkyl |
| c | Halogen | halogen | C1–C6 alkoxy |
| d | Halogen | halogen | nitro |
| e | Halogen | halogen | carboxyl |
| f | Halogen | C1–C6 alkyl | C1–C6 alkyl |
| g | Halogen | C1–C6 alkoxy | C1–C6 alkoxy |
| h | C1–C6 alkyl | C1–C6 alkyl | C1–C6 alkyl |
| i | C1–C6 alkoxy | C1–C6 alkoxy | C1–C6 alkoxy |
| j | C1–C6 alkyl | C1–C6 alkyl | nitro |
| k | C1–C6 alkoxy | C1–C6 alkoxy | nitro |

According to certain embodiments, the benzyl and/or styryl aromatic nuclei are tetra-substituted, that is, only one of $R_1$ through $R_5$ is hydrogen, and/or only one of $R_6$ through $R_{10}$ is hydrogen. Representative combinations of substituents are set forth in Table 2:

TABLE 2

Tetra-Substitution

| | | | | |
|---|---|---|---|---|
| a | Halogen | halogen | halogen | halogen |
| b | Halogen | halogen | halogen | C1–C6 alkyl |
| c | Halogen | halogen | halogen | C1–C6 alkoxy |
| d | Halogen | halogen | halogen | nitro |
| e | Halogen | halogen | C1–C6 alkyl | C1–C6 alkyl |
| f | Halogen | halogen | C1–C6 alkoxy | C1–C6 alkoxy |
| g | C1–C6 alkyl | C1–C6 alkyl | C1–C6 alkyl | nitro |
| h | C1–C6 alkoxy | C1–C6 alkoxy | C1–C6 alkoxy | nitro |

According to other embodiments, the benzyl and/or styryl aromatic nuclei are penta-substituted, preferably with halogen, most preferably with the same halogen, for example, penta-substitution with fluorine.

The pattern of substitution with respect to the position of the substituents on the benzyl or styryl nuclei may comprise any pattern of substitution. For example, tri-substitution may comprise substitution at positions 2, 3 and 4, positions 2, 4 and 5, or positions 2, 4 and 6, for example. Likewise, the pattern of tetra-substitution may comprise, for example, substitution at positions 2, 3, 4 and 5, or positions 2, 3, 5 and 6.

According to certain preferred embodiments, the 4-position of the benzyl and/or styryl nuclei is substituted, that is, $R_3$ and/or $R_8$ are other than hydrogen. Preferably, $R_3$ and/or $R_8$ are halogen or C1–C6 alkoxy.

According to one such embodiment of 4-position substitution, the benzyl nucleus is mono-substituted at its 4 position. $R_3$ is selected from the group consisting of halogen, C1–C6 alkoxy, nitro, cyano hydroxyl, phosphonato, amino, sulfamyl, acetoxy, and dimethylamino (C2–C6 alkoxy) and trifluoromethyl; $R_1$, $R_2$, $R_4$ and $R_5$ are hydrogen; and $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, wherein at least three of $R_6$, $R_7$, $R_8$, $R_9$ and $R_{10}$ are other than hydrogen. Particularly preferred are compounds according to formula IV, and pharmaceutically acceptable salts thereof:

IV wherein $R_3$ and $R_8$ are independently selected from the group consisting of halogen, C1–C6 alkoxy, nitro, cyano, hydroxyl, phosphonato, amino, sulfamyl, acetoxy, dimethylamino(C2–C6 alkoxy) and trifluoromethyl. $R_6$ and $R_{10}$ are independently selected from the group consisting of C1–C6 alkoxy, hydroxyl, phosphonato, amino, sulfamyl, acetoxy and dimethylamino(C2–C6 alkoxy). In some embodiments, $R_3$ and $R_8$ are independently selected from the group consisting of halogen and C1–C6 alkoxy. $R_6$ and $R_{10}$ are preferably C1–C6 alkoxy, more preferably C1–C3 alkoxy. In some embodiments, $R_3$, $R_6$, $R_8$, and $R_{10}$ are C1–C6 alkoxy, preferably C1–C3 alkoxy.

According to another such embodiment of 4-position substitution in formula I, $R_3$ is C1–C6 alkoxy; and two of $R_1$, $R_2$, $R_4$ and $R_5$ are also C1–C6 alkoxy, with the remainder of $R_1$, $R_2$, $R_4$ and $R_5$ being hydrogen, that is, the benzyl nucleus is trisubstituted with C1–C6 alkoxy groups. $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

In each of the above embodiments containing alkoxy substituents on the benzyl and/or styryl nucleus, the alkoxy group is preferably a C1–C3 alkoxy group, must preferably methoxy.

Without wishing to be bound by any theory, it is believed that the compounds affect the MAPK signal transduction pathway, thereby affecting tumor cell growth and viability. This cell growth inhibition is associated with regulation of the ERK and JNK types of MAPK. Without wishing to be bound by any theory, the styryl sulfones of the present invention may block the phosphorylating capacity of ERK-2.

The compounds of the invention have been shown to inhibit the proliferation of tumor cells by inducing cell death. The compounds are believed effective against a broad range of tumor types, including but not limited to the following: breast, prostate, ovarian, lung, colorectal, brain (i.e., glioma) and renal. The compounds are also believed effective against leukemic cells. The compounds do not kill normal cells in concentrations at which tumor cells are killed.

The compounds are also believed useful in the treatment of non-cancer proliferative disorders, including but not limited to the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

Treatment of this broad range of tumor cells with the styryl benzylsulfone compounds of the invention leads to inhibition of cell proliferation and induction of apoptotic cell death.

Tumor cells treated with the compounds of the invention accumulate in the G2/M phase of the cell cycle. As the cells exit the G2/M phase, they appear to undergo apoptosis. Treatment of normal cells with the styryl sulfones does not result in apoptosis.

(E)-Styryl benzylsulfones may be prepared by Knoevenagel condensation of aromatic aldehydes with benzylsulfonyl acetic acids. The procedure is described by Reddy et al., *Acta. Chim. Hung.* 115:269–71 (1984); Reddy et al., *Sulfur Letters* 13:83–90 (1991); Reddy et al., *Synthesis No.* 4, 322–323 (1984); and Reddy et al., *Sulfur Letters* 7:43–48 (1987), the entire disclosures of which are incorporated herein by reference.

According to the Scheme 1 below, $R_a$ and $R_b$ each represent from zero to five substituents on the depicted aromatic nucleus. The benzyl thioacetic acid B is formed by the reaction of sodium thioglycollate and a benzyl chloride A. The benzyl thioacetic acid B is then oxidized with 30% hydrogen peroxide to give a corresponding benzylsulfonyl acetic acid C. Condensation of the benzylsulfonyl acetic acid C with an aromatic aldehyde D via a Knoevenagel reaction in the presence of benzylamine and glacial acetic acid yields the desired (E)-styryl benzylsulfone E.

oxidation with 30% hydrogen peroxide (0.12 mol) in glacial acetic acid (125 ml) by refluxing for 1 hour. The contents are cooled and poured onto crushed ice. The separated solid is recrystalized from hot water to give the corresponding pure benzylsulfonylacetic acid.

Part B. A mixture of the benzylsulfonyl acetic acid (10 mmol), an appropriately substituted or unsubstituted aromatic aldehyde (10 mmol), and benzylamine (200 ml) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields styryl benzylsulfones as a solid material.

According to an alternative to Part A, the appropriate benzylsulfonylacetic acids may be generated by substituting a thioglycollate $HSCH_2COOR$ for thioglycollic acid, where R is an alkyl group, typically C1–C6 alkyl. This leads to the formation of the alkylbenzylthioacetate intermediate (F),

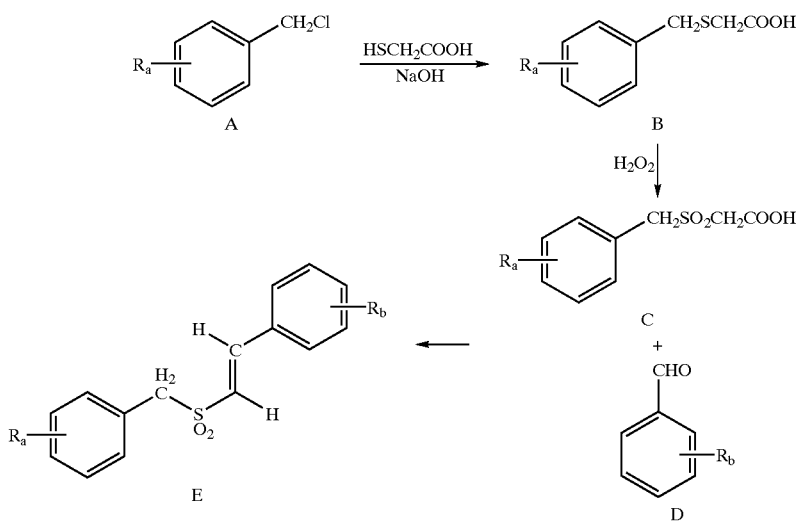

Scheme 1

The following is a more detailed two-part synthesis procedure for preparing (E)-styryl benzylsulfones according to the above scheme.

General Procedure 1: Synthesis (E)-Styryl Benzylsulfones

Part A. To a solution of (8 g, 0.2 mol) sodium hydroxide in methanol (200 ml), thioglycollic acid (0.1 mol) is added slowly and the precipitate formed is dissolved by stirring the contents of the flask. Then an appropriately substituted or unsubstituted benzyl chloride (0.1 mol) is added stepwise and the reaction mixture is refluxed for 2–3 hours. The cooled contents are poured onto crushed ice and neutralized with dilute hydrochloric acid (200 ml). The resulting corresponding benzylthioacetic acid (0.1 mol) is subjected to

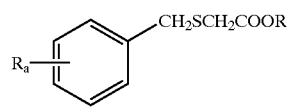

which is then converted to the corresponding benzyl thioacetic acid B by alkaline or acid hydrolysis.

(Z)-Styryl benzylsulfones are prepared by the nucleophilic addition of the appropriate thiol to substituted phenylacetylene with subsequent oxidation of the resulting sulfide by hydrogen peroxide to yield the Z-styryl benzylsulfone. The procedure is generally described by Reddy et al., *Sulfur Letters* 13:83–90 (1991), the entire disclosure of which is incorporated herein as a reference.

In the first phase of the synthesis, a substituted or unsubstitued sodium benzylthiolate, prepared from an appropriate substituted or unsubstitued sodium benzyl mercaptan, is allowed to react with the appropriate substituted phenylacetylene forming the pure Z-isomer of the corresponding substituted (Z)-styryl benzylsulfide in good yield. In the second step of the synthesis, the substituted (Z)-styryl benzylsulfide intermediate is oxidized to the corresponding sulfone in the pure Z-isomeric form by treatment with an oxidizing agent, such as hydrogen peroxide.

The following is a more detailed two-part synthesis procedure for preparing the substituted (Z)-styryl benzylsulfones. It may be appreciated that at least one of the starting styrene and sodium benzyl mercaptan are at least trisubstituted, in order to form compounds according to formula I.

General Procedure 2: Synthesis of Substituted (Z)-styryl Benzylsulfones

A. To a cooled stirred solution (40° C.) of a substituted or unsubstituted styrene (0.5 mol) in chloroform (200 ml) is added dropwise a solution of bromine (0.5 mol) in chloroform (100 ml). After the addition is complete, the contents of the flask are stirred for an additional 30 minutes. Removal of chloroform in rotavapor yields a crystalline solid of a 1,2-dibromoaryl ethane.

B. A solution of potassium hydroxide (85 g) in rectified spirit (400 ml) is cooled to room temperature (25° C.) and the above 1,2-dibromoaryl ethane (0.33 mol) is added in portions to control the exothermic reaction. After the addition is complete, the reaction mixture is heated to reflux for 6 hours. The contents are then cooled and poured into water (1000 ml). The separated substituted or unsubstituted phenylacetylene is purified either by distillation (in case of liquids) or recrystallization (In case of solids).

C. To a refluxing methanolic solution of a substituted or unsubstituted sodium benzylthiolate prepared from 460 mg (0.02 g atom) of (i) sodium, (ii) substituted or unsubstituted sodium benzyl mercaptan (0.02 mol) and (iii) 80 ml of absolute methanol, is added a freshly distilled substituted or unsubstituted phenylacetylene. The mixture is refluxed for 20 hours, cooled and then poured on crushed ice. The crude product is filtered, dried and recrystallized from methanol or aqueous methanol to yield pure substituted (Z)-styryl benzylsulfide.

D. An ice cold solution of a substituted (Z)-styryl benzylsulfide (3 g) in 30 ml of glacial acetic acid is treated with 7.5 ml of 30% hydrogen peroxide. The reaction mixture is refluxed for 1 hour and poured onto crushed ice. The solid separated is filtered, dried and recrystallized from 2-propanol to yield a pure substituted (Z)-styryl benzylsulfone. The purity of the compound is ascertained by TLC and geometrical configuration is assigned by IR and NMR spectral data.

The benzyl thioacetic acid B, benzylsulfonyl acetic acid C, and alkylbenzylthioacetate (F) are novel intermediates which form another aspect of the invention. Accordingly, intermediate compounds useful in the synthesis of the substituted benzylstyryl sulfones comprise the substituted benzylthioacetic acids and esters of formulae II, and the substituted benzylsulfonyl acetic acids of formula III,

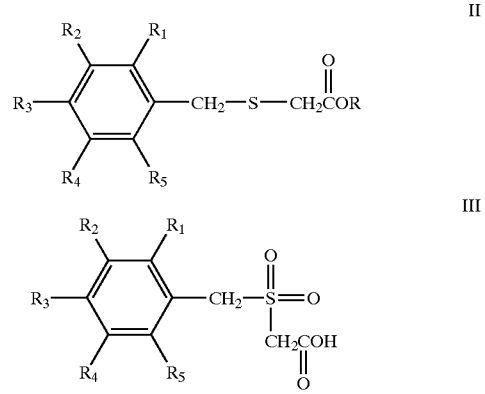

wherein:

R is H or C1–C6 alkyl;

at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

According to preferred embodiments of the intermediates of formulae II and III, at least three of $R_1$, $R_2$, $R_3$, $R_4$ and $R_5$ are independently selected from the group consisting of halogen, C1–C6 alkyl and C1–C6 alkoxy, and the balance of said $R_1$, $R_2$, $R_3$, $R_4$ and $R_5$ are independently selected from the group consisting of hydrogen, halogen, C1–C6 alkyl, C1–C6 alkoxy. C1–C3 alkyl and C1–C3 alkoxy are the preferred alkyl and alkoxy substituents, with methyl and methoxy being most preferred. According of other preferred embodiments, all of $R_1$, $R_2$, $R_3$, $R_4$ and $R_5$ are halogen, preferably the same halogen, or all are C1–C6 alkoxy, most preferably C1–C3 alkoxy, most preferably methoxy.

Other novel intermediates useful in preparing the compounds of formula I comprise the compounds of formulae V

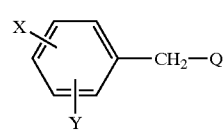

wherein:

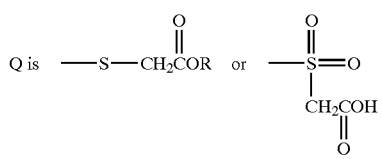

R is H or C1–C6 alkyl; and

X and are Y independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl;

provided:
  when Y is hydrogen, X may not be hydrogen, 4-chloro, 4-bromo, 4-fluoro or 4-alkoxy.

In one embodiment, X and Y are as defined as above, with the further provision that
  when Y is hydrogen, X may not be 4-trifluoromethyl, 4-nitro or 4-cyano; and
  when X is 4-chloro, Y may not be 2-chloro or 3-chloro.

According to a preferred embodiment, intermediates are provided according to formula V wherein Y is hydrogen and X is selected from the group consisting of 4-hydroxy, 4-amino and 4-sulfamyl.

The intermediates may be prepared according to General procedure 1, Part A, above.

Representative intermediates prepared according to the present invention, and their respective melting points, include the following (ND=melting point not done):

2,4-dichlorobenzylthioacetic acid, 69–71° C.;
2,4-dichlorobenzylsulfonylacetic acid, 178–180° C.;
4-iodobenzylthioacetic acid, 79–81° C.;
4-iodobenzylsulfonylacetic acid 193–196° C.;
2-methoxybenzylthioacetic acid, liquid;
2-methoxybenzylsulfonylacetic acid, liquid;
2,4-dimethoxy benzylthioacetic acid, ND;
2,4-dimethoxybenzylsulfonylacetic acid, ND;
4-cyanobenzylthioacetic acid, 80–82° C.;
4-cyanobenzylsulfonylacetic acid, 211–213° C.;
4-trifluoromethylbenzylthiolacetic acid, ND;
4-trifluoromethylbenzylsulfonylacetic acid, 162–164° C.;
2,3,4-trimethoxybenzylthioacetic acid, liquid;
2,3,4-trimethoxybenzylsulfonylacetic acid, 140–144° C.;
3,4,5-trimethoxybenzylthioacetic acid, ND;
3,4,5-trimethoxybenzylsulfonylacetic acid, 165–167° C.;
2,4,6-trimethoxybenzylthioacetic acid, ND;
2,4,6-trimethoxybenzylsulfonylacetic acid, ND;
2-nitro-4,5-dimethoxybenzylthioacetic acid, ND;
2-nitro-4,5-dimethoxybenzylsulfonylacetic acid, 137–140° C.;
3,5-dimethoxybenzylthioacetic acid, liquid;
3,5-dimethoxybenzylsulfonylacetic acid, liquid;
2-methoxy-5-nitrobenzylthioacetic acid, liquid;
2-methoxy-5-nitrobenzylsulfonylacetic acid, 158–160° C.;
4-hydroxybenzylthioacetic acid, ND;
4-hydroxybenzylsulfonylacetic acid, ND;
1,2,3,4,5-pentafluorobenzylthioacetic acid, 68–70° C.; and
1,2,3,4,5-pentafluorobenzylsulfonylacetic acid, 108–110° C.

The present invention is also directed to isolated optical isomers of compounds according to formula I. Certain compounds may have one or more chiral centers. By "isolated" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof. Isolated optical isomers may be purified from racemic mixtures by well-known chiral separation techniques. According to one such method, a racemic mixture of a compound having the structure of formula I, or chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

The styryl benzylsulfone compounds of the present invention may be derivatized with a chemical group to permit conjugation to a carrier molecule, for the purpose of raising antibodies to the styryl sulfones. Suitable derivatizing chemistries are well-known to those skilled in the art. Preferably, the derivative comprises a carboxylic acid derivative. The carrier may comprise any molecule sufficiently large to be capable of generating an immune response in an appropriate host animal. One such preferred carrier is keyhole limpet haemocyanin (KLH).

The compounds of the present invention may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples. For each (E) configuration compound, the substituted benzylsulfonyl acetic acid was made according to Part A of General Procedure 1: Synthesis (E)-Styryl Benzylsulfones, above. Some of the styryl benzylsulfone compounds were recrystalized from 2-propanol and the purity was checked by thin layer chromatography. Each (Z) configuration compound is prepared by following General Procedure 2: Synthesis (Z)-Styryl Benzylsulfones, above. For brevity, only the principal reactants are listed in each example, it being understood that the principal reactants are made from precursors as set forth in the General Procedure, and then combined under the conditions set forth in the General Procedure.

EXAMPLE 1

(E)-2,3,4,5,6-Pentafluorostyryl-4-fluorobenzylsulfone

A solution of 4-fluorobenzylsulfonylacetic acid (10 mmol) and pentafluorobenzaldehyde (10 mmol) was subjected to the General Procedure 1, Part B. The title compound, melting point 133–136° C., was obtained in 80% yield.

EXAMPLE 2

(E)-2,3,4,5,6-Pentafluorostyryl-4-chlorobenzylsulfone

A solution of 4-chlorobenzylsulfonylacetic acid (10 mmol) and pentafluorobenzaldehyde (10 mmol) was subjected to the General Procedure 1, Part B. The title compound, melting point 147–148° C., was obtained in 82% yield.

EXAMPLE 3

(E)-2,3,4,5,6-Pentafluorostyryl-4-bromobenzylsulfone

A solution of 4-bromobenzylsulfonylacetic acid (10 mmol) and pentafluorobenzaldehyde (10 mmol) was subjected to the General Procedure 1, Part B. The title compound, melting point 163–164° C., was obtained in 85% yield.

EXAMPLE 4

(E)-4-Fluorostyryl-2,3,4,5,6-pentafluorobenzylsulfone

A solution of pentafluorobenzylsulfonylacetic acid (10 mmol) and 4-fluorobenzaldehyde (10 mmol) was subjected to the General Procedure 1, Part B. The title compound, melting point 133–136° C., was obtained in 78% yield.

EXAMPLE 5

(E)-4-Chlorostyryl-2,3,4,5,6-pentafluorobenzylsulfone

A solution of pentafluorobenzylsulfonylacetic acid (10 mmol) and 4-chlorobenzaldehyde (10 mmol) was subjected

EXAMPLE 6

(E)-4-Bromostyryl-2,3,4,5,6-pentafluorobenzylsulfone

A solution of pentafluorobenzylsulfonylacetic acid (10 mmol) and 4-bromobenzaldehyde (10 mmol) was subjected to the General Procedure 1, Part B. The title compound, melting point 176–177° C., was obtained in 92% yield.

EXAMPLE 7

(E)-2,3,4,5,6-Pentafluorostyryl-3,4-dichlorobenzylsulfone

A solution of 3,4-dichlorobenzylsulfonylacetic acid (10 mmol) and pentafluorobenzaldehyde (10 mmol) was subjected to the General Procedure 1, Part B. The title compound, melting point 171–173° C., was obtained in 84% yield.

EXAMPLE 8

(E)-2,3,4,5,6-Pentafluorostyryl-2,3,4,5,6-pentafluorobenzylsulfone

A solution of pentafluorobenzylsulfonylacetic acid (10 mmol) and pentafluorobenzaldehyde (10 mmol) was subjected to the General Procedure 1, Part B. The title compound, melting point 137–139° C., was obtained in 84% yield.

EXAMPLE 9

(E)-2,3,4,5,6-Pentafluorostyryl-4-iodobenzylsulfone

A solution of 4-iodobenzylsulfonylacetic acid (10 mmol) and pentafluorobenzaldehyde (10 mmol) was subjected to the General Procedure 1, Part B. The title compound, melting point 178–181° C., was obtained in 51% yield.

EXAMPLE 10

(E)-2-Hydroxy-3,5-dinitrostyryl-4-fluorobenzylsufone

A solution of 4-fluorobenzylsulfonylacetic acid (10 mmol) and 2-hydroxy-3,5-dinitrobenzaldehyde (10 mmol) was subjected to the General Procedure 1, Part B. The title compound, melting point 211–212° C., was obtained in 54% yield.

EXAMPLE 11

(E)-2-Hydroxy-3,5-dinitrostyryl-4-bromobenzylsufone

A solution of 4-bromobenzylsulfonylacetic acid (10 mmol) and 2-hydroxy-3,5-dinitrobenzaldehyde (10 mmol) was subjected to the General Procedure 1, Part B. The title compound, melting point 207–209° C., was obtained in 52% yield.

EXAMPLE 12

(E)-2-Hydroxy-3,5-dinitrostyryl-4-chlorobenzylsufone

A solution of 4-chlorobenzylsulfonylacetic acid (10 mmol) and 2-hydroxy-3,5-dinitrobenzaldehyde (10 mmol) was subjected to the General Procedure 1, Part B. The title compound, melting point 204–205° C., was obtained in 51% yield.

EXAMPLE 13

(E)-2-Hydroxy-3,5-dinitrostyryl-2,4-dichlorobenzylsufone

A solution of 2,4-chlorobenzylsulfonylacetic acid (10 mmol) and 2-hydroxy-3,5-dinitrobenzaldehyde (10 mmol) was subjected to the General Procedure 1, Part B. The title compound, melting point 212–213° C., was obtained in 56% yield.

EXAMPLE 14

(E)-2,4,6-Trimethoxystyryl-4-methoxybenzylsulfone

A solution of 4-methoxybenzylsulfonylacetic acid (10 mmol) and 2,4,6-trimethoxybenzaldehyde (10 mmol) was subjected to the General Procedure 1, Part B. The title compound, melting point 142–144° C., was obtained in 52% yield.

EXAMPLE 15

(E)-3-Methyl-2,4-dimethoxystyryl-4-methoxybenzylsulfone

A solution of 4-methoxybenzylsulfonylacetic acid (10 mmol) and 3-methyl-2,4-dimethoxybenzaldehye (10 mmol) was subjected to the General Procedure 1, Part B. The title compound, melting point 160–161° C., was obtained in 52% yield.

EXAMPLE 16

(E)-3,4,5-Trimethoxystyryl-4-methoxybenzylsulfone

A solution of 4-methoxybenzylsulfonylacetic acid (10 mmol) and 3,4,5-trimethoxybenzaldehyde (10 mmol) was subjected to the General Procedure 1, Part B. The title compound, melting point 138–140° C., was obtained in 54% yield.

EXAMPLE 17

(E)-3,4,5-Trimethoxystyryl-2-nitro-4,5-dimethoxybenzylsulfone

A solution of 2-nitro-4,5-dimethoxybenzylsulfonylacetic acid (10 mmol) and 3,4,5-trimethoxybenzaldehyde (10 mmol) was subjected to the General Procedure 1, Part B. The title compound was obtained.

EXAMPLE 18

(E)-2,4,6-Trimethoxystyryl-2-nitro-4,5-dimethoxybenzylsufone

A solution of 2-nitro-4,5-dimethoxybenzylsulfonylacetic acid (10 mmol) and 2,4,6-trimethoxybenzaldehyde (10 mmol) was subjected to the General Procedure 1, Part B. The title compound was obtained.

EXAMPLE 19

(E)3-Methyl-2,4-dimethoxystyryl-2-nitro-4,5-dimethoxybezylsulfone

A solution of 2-nitro-4,5-dimethoxybenzylsulfonylacetic acid (10 mmol) and 3-methyl-2,4-dimethoxybenzaldehyde (10 mmol) was subjected to the General Procedure 1, Part B. The title compound was obtained.

EXAMPLE 20

(E)-2,3,4-Trifluorostyryl-4-fluorobenzylsulfone

A solution of 4-fluorobenzylsulfonylacetic acid (10 mmol) and 2,3,4-trifluorobenzaldehyde (10 mmol) was subjected to the General Procedure 1, Part B. The title compound, melting point 128–129° C., was obtained in 72% yield.

EXAMPLE 21

(E)-2,3,4-Trifluorostyryl-4-chlorobenzylsulfone

A solution of 4-chlorobenzylsulfonylacetic acid (10 mmol) and 2,3,4-trifluorobenzaldehyde (10 mmol) was subjected to the General Procedure 1, Part B. The title compound, melting point 141–142° C., was obtained in 78% yield.

EXAMPLE 22

(E)-2,6-Dimethoxy-4-hydroxystyryl-4-methoxybenzylsulfone

A solution of 4-methoxybenzylsulfonylacetic acid (10 mmol) and 2,6-dimethoxy-4-hydroxybenzaldehyde (10 mmol) was subjected to the General Procedure 1, Part B. The title compound, melting point 134–136° C., was obtained in 58% yield.

EXAMPLE 23

(E)-2,3,5,6-Tetrafluorostyryl-4-methoxybenzylsulfone

A solution of 4-methoxybenzylsulfonylacetic acid (10 mmol) and 2,3,5,6-tetrafluorobenzaldehyde (10 mmol) was subjected to the General Procedure 1, Part B. The title compound, melting point 154–156° C., was obtained in 56% yield.

EXAMPLE 24

(E)-2,4,5-Trimethoxystyryl-4-methoxybenzylsulfone

A solution of 4-methoxybenzylsulfonylacetic acid (10 mmol) and 2,4,5-trimethoxybenzaldehyde (10 mmol) was subjected to the General Procedure 1, Part B. The title compound, melting point 146–148° C., was obtained in 66% yield.

EXAMPLE 25

(E)-2,3,4-Trimethoxystyryl-4-methoxybenzylsulfone

A solution of 4-methoxybenzylsulfonylacetic acid (10 mmol) and 2,3,4-trimethoxybenzaldehyde (10 mmol) was subjected to the General Procedure 1, Part B. The title compound, melting point 154–156° C., was obtained in 52% yield.

EXAMPLE 26

(E)-3-Nitro-4-hydroxy-5-methoxystyryl-4-methoxybenzylsulfone

A solution of 4-methoxybenzylsulfonylacetic acid (10 mmol) and 3-nitro-4-hydroxy-5-methoxybenzaldehyde (10 mmol) was subjected to the General Procedure 1, Part B. The title compound, melting point 203–205° C., was obtained in 56% yield.

EXAMPLE 27

(E)-3,4-Dimethoxy-6-nitrostyryl-4-methoxybenzylsulfone

A solution of 4-methoxybenzylsulfonylacetic acid (10 mmol) and 3,4-dimethoxy-6-nitrobenzaldehyde (10 mmol) was subjected to the General Procedure 1, Part B. The title compound, melting point 139–141° C., was obtained in 54% yield.

EXAMPLE 28

(E)-3,4-Dimethoxy-5-iodostyryl-4-methoxybenzylsulfone

A solution of 4-methoxybenzylsulfonylacetic acid (10 mmol) and 3,4-dimethoxy-5-iodobenzaldehyde (10 mmol) was subjected to the General Procedure 1, Part B. The title compound, melting point 160–161° C., was obtained in 58% yield.

EXAMPLE 29

(E)-2,6-Dimethoxy-4-fluorostyryl-4-methoxybenzylsulfone

A solution of 4-methoxybenzylsulfonylacetic acid (10 mmol) and 2,6-dimethoxy-4-fluorobenzaldehyde (10 mmol) was subjected to the General Procedure 1, Part B. The title compound, melting point 146–148° C., was obtained in 55% yield.

EXAMPLE 30

(E)-2-Hydroxy-4,6-dimethoxystyryl-4-methoxybenzylsulfone

A solution of 4-methoxybenzylsulfonylacetic acid (10 mmol) and 2-hydroxy-4,6-dimethoxybenzaldehyde (10 mmol) was subjected to the General Procedure 1, Part B. The title compound was obtained.

EXAMPLE 31

(E)-2,4,6-Trimethylstyryl-4-methoxybenzylsulfone

A solution of 4-methoxybenzylsulfonylacetic acid (10 mmol) and 2,4,6-trimethylbenzaldehyde (10 mmol) was subjected to the General Procedure 1, Part B. The title compound, melting point 97–99° C., was obtained in 51% yield.

EXAMPLE 32

(E)-2,4,6-Trimethoxystyryl-4-chlorobenzylsulfone

A solution of 4-chlorobenzylsulfonylacetic acid (10 mmol) and 2,4,6-trimethoxybenzaldehyde (10 mmol) was subjected to the General Procedure 1, Part B. The title compound, melting point 181–183° C., was obtained in 54% yield.

EXAMPLE 33

(E)-2,6-Dimethoxy-4-fluorostyryl-4-chlorobenzylsulfone

A solution of 4-chlorobenzylsulfonylacetic acid (10 mmol) and 2,6-dimethoxy-4-fluorobenzaldehyde (10 mmol)

EXAMPLE 34

(E)-2-Hydroxy-4,6-dimethoxystyryl-4-chlorobenzylsulfone

A solution of 4-chlorobenzylsulfonylacetic acid (10 mmol) and 2-hydroxy-4,6-dimethoxybenzaldehyde (10 mmol) was subjected to the General Procedure 1, Part B. The title compound was obtained.

EXAMPLE 35

(E)-2,4,6-Trimethoxystyryl-4-bromobenzylsulfone

A solution of 4-bromobenzylsulfonylacetic acid (10 mmol) and 2,4,6-trimethoxybenzaldehyde (10 mmol) was subjected to the General Procedure 1, Part B. The title compound, melting point 178–181° C., was obtained in 54% yield.

EXAMPLE 36

(E)-2,6-Dimethoxy-4-fluorostyryl-4-bromobenzylsulfone

A solution of 4-bromobenzylsulfonylacetic acid (10 mmol) and 2,6-dimethoxy-4-fluorobenzaldehyde (10 mmol) was subjected to the General Procedure 1, Part B. The title compound, melting point 116–118° C., was obtained in 58% yield.

EXAMPLE 37

(E)-2,4,6-Trimethoxystyryl-2,3,4-trimethoxybenzylsulfone

A solution of 2,3,4-trimethoxybenzylsulfonylacetic acid (10 mmol) and 2,4,6-trimethoxybenzaldehyde (10 mmol) was subjected to the General Procedure 1, Part B. The title compound, melting point 94–96° C., was obtained in 52% yield.

EXAMPLE 38

(E)-2,6-Dimethoxystyryl-2,3,4-trimethoxybenzylsulfone

A solution of 2,3,4-trimethoxybenzylsulfonylacetic acid (10 mmol) and 2,6-dimethoxybenzaldehyde (10 mmol) was subjected to the General Procedure 1, Part B. The title compound, melting point 110–112° C., was obtained in 54% yield.

EXAMPLE 39

(E)-2,4,6-Trimethoxystyryl-,3,4,5-trimethoxybenzylsulfone

A solution of 3,4,5-trimethoxybenzylsulfonylacetic acid (10 mmol) and 2,4,6-trimethoxybenzaldehyde (10 mmol) was subjected to the General Procedure 1, Part B. The title compound, melting point 151–153° C., was obtained in 54% yield.

EXAMPLE 40

(E)-2,6-Dimethoxystyryl-3,4,5-trimethoxybenzylsulfone

A solution of 3,4,5-trimethoxybenzylsulfonylacetic acid (10 mmol) and 2,6-dimethoxybenzaldehyde (10 mmol) was subjected to the General Procedure 1, Part B. The title compound, melting point 146–149° C., was obtained in 53% yield.

EXAMPLE 41

(E)-4-Fluorostyryl-2,3,4-trimethoxybenzylsulfone

A solution of 2,3,4-trimethoxybenzylsulfonylacetic acid (10 mmol) and 4-fluorobenzaldehyde (10 mmol) was subjected to the General Procedure 1, Part B. The title compound, melting point 96–99° C., was obtained in 68% yield.

EXAMPLE 42

(Z)-2,4,6-trifluorostyryl-4-methylbenzylsulfone

A solution of 2,4,6-trifluorophenylacetylene (0.02 mol), 4-methylbenzyl mercaptan (0.02 mol) and metallic sodium (0.02 g atom) is subjected to General Procedure 2 to form (Z)-2,4,6-trifluorostyryl-4-methylbenzylsulfide. The title compound is obtained following oxidation of the sulfide, according to General Procedure 2.

EXAMPLE 43

(Z)-pentafluorostyryl-4-chlorobenzylsulfone

A solution of pentafluorophenylacetylene (0.02 mol), 4-chlorobenzyl mercaptan (0.02 mol) and metallic sodium (0.02 g atom) is subjected to General Procedure 2 to form (Z)-pentafluorostyryl-4-chlorobenzylsulfide. The title compound is obtained following oxidation of the sulfide, according to General Procedure 2.

EXAMPLE 44

(Z)-pentafluorostyryl-4-methoxybenzylsulfone

A solution of pentafluorophenylacetylene (0.02 mol), 4-methoxybenzyl mercaptan (0.02 mol) and metallic sodium (0.02 g atom) is subjected to General Procedure 2 to form (Z)-pentafluorostyryl-4-methoxybenzylsulfide. The title compound is obtained following oxidation of the sulfide, according to General Procedure 2.

EXAMPLE 45

(Z)-pentafluorostyryl-2,3,4-trimethoxybenzylsulfone

A solution of pentafluorophenylacetylene (0.02 mol), 2,3,4-trimethoxybenzyl mercaptan (0.02 mol) and metallic sodium (0.02 g atom) is subjected to General Procedure 2 to form (Z)-pentafluorostyryl-2,3,4-trimethoxybenzylsulfide. The title compound is obtained following oxidation of the sulfide, according to General Procedure 2.

EXAMPLE 46

(Z)-pentafluorostyryl-3,4,5-trimethoxybenzylsulfone

A solution of pentafluorophenylacetylene (0.02 mol), 3,4,5-trimethoxybenzyl mercaptan (0.02 mol) and metallic sodium (0.02 g atom) is subjected to General Procedure 2 to form (Z)-pentafluorostyryl-3,4,5-trimethoxybenzylsulfide. The title compound is obtained following oxidation of the sulfide, according to General Procedure 2.

EXAMPLE 47

(Z)-pentafluorostyryl-2,4,6-trimethoxybenzylsulfone

A solution of pentafluorophenylacetylene (0.02 mol), 2,4,6-trimethoxybenzyl mercaptan (0.02 mol) and metallic sodium (0.02 g atom) is subjected to General Procedure 2 to form (Z)-pentafluorostyryl-2,4,6-trimethoxybenzylsulfide. The title compound is obtained following oxidation of the sulfide, according to General Procedure 2.

EXAMPLE 48

(Z)-3-methoxy-4-acetoxystyryl-2,4,5-trimethoxybenzylsulfone

A solution of 3-methoxy-4-acetoxyphenylacetylene (0.02 mol), 2,4,5-trimethoxybenzyl mercaptan (0.02 mol) and metallic sodium (0.02 g atom) is subjected to General Procedure 2 to form (Z)-3-methoxy-4-acetoxystyryl-2,4,5-trimethoxybenzylsulfide. The title compound is obtained following oxidation of the sulfide, according to General Procedure 2.

EXAMPLE 49

(Z)-3,4-dihydroxystyryl-2,4,6-trimethoxybenzylsulfone

A solution of 3,4-dihydroxyphenylacetylene (0.02 mol), 2,4,6-trimethoxybenzyl mercaptan (0.02 mol) and metallic sodium (0.02 g atom) is subjected to General Procedure 2 to form (Z)-3,4-dihydroxystyryl-2,4,6-trimethoxybenzylsulfide. The title compound is obtained following oxidation of the sulfide, according to General Procedure 2.

EXAMPLE 50

(Z)-2,4,6-trifluorostyryl-4-nitrobenzylsulfone

A solution of 2,4,6-trifluorophenylacetylene (0.02 mol), 4-nitrobenzyl mercaptan (0.02 mol) and metallic sodium (0.02 g atom) is subjected to General Procedure 2 to form (Z)-2,4,6-trifluorostyryl-4-nitrobenzylsulfide. The title compound is obtained following oxidation of the sulfide, according to General Procedure 2.

EXAMPLE 51

(Z)-2-hydroxystyryl-2,4,6-trimethoxybenzylsulfone

A solution of 2-hydroxyphenylacetylene (0.02 mol), 2,4,6-trimethoxybenzyl mercaptan (0.02 mol) and metallic sodium (0.02 g atom) is subjected to General Procedure 2 to form (Z)-2-hydroxystyryl-2,4,6-trimethoxybenzylsulfide. The title compound is obtained following oxidation of the sulfide, according to General Procedure 2.

EXAMPLE 52

(Z)-2-phosponatostyryl-2,3,4-trimethoxybenzylsulfone

A solution of 2-phosphonatophenylacetylene (0.02 mol), 2,3,4-trimethoxybenzyl mercaptan (0.02 mol) and metallic sodium (0.02 g atom) is subjected to General Procedure 2 to form (Z)-2-phosponatostyryl-2,3,4-trimethoxybenzylsulfide. The title compound is obtained following oxidation of the sulfide, according to General Procedure 2.

EXAMPLE 53

(Z)-4-phosponatostyryl-2,4,6-trimethoxybenzylsulfone

A solution of 4-phosphonatophenylacetylene (0.02 mol), 2,3,4-trimethoxybenzyl mercaptan (0.02 mol) and metallic sodium (0.02 g atom) is subjected to the General Procedure to form (Z)-4-phosponatostyryl-2,4,6-trimethoxybenzylsulfide. The title compound is obtained following oxidation of the sulfide, according to the General Procedure.

Effect of (E)-Styryl Benzylsulfones on Tumor Cell Lines—Protocol 1

A. Cells

The effect of the (E)-styryl benzylsulfones on normal fibroblasts and on tumor cells of prostate, colon, lung and breast origin was examined utilizing the following cell lines: prostate tumor cell line DU-145; colorectal carcinoma cell line DLD-1; non-small cell lung carcinoma cell line H157; and breast tumor cell line BT-20. BT-20 is an estrogen-unresponsive cell line. NIH/3T3 and HFL are normal murine and human fibroblasts, respectively. BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH3T3 and HFL cells were grown in DMEM containing 10% calf serum supplemented with penicillin and streptomycin. All cell cultures were maintained at 37° C. in a humidified atmosphere of 5% $CO_2$.

B. Treatment with Styryl Benzylsulfones and Viability Assay

Cells were treated with test compound at 2.5 micromolar concentration and cell viability was determined after 96 hours by the Trypan blue exclusion method. Each compound tested (Exs. 1–16, 20, 21, 23–29, 31–33 and 35–40) showed activity, inducing cell death against all tumor cell lines, in at least 5–10% of the treated cells.

Normal cells HFL and NIH 3T3 were treated with the same compounds under the same conditions of concentration and time. The normal cells displayed 5% growth inhibition but no appreciable cell death.

Effect of (Z)-Styryl Benzylsulfones on Tumor Cell Lines—Protocol 2

In a variation of the above assay, the effect of the (Z)-styryl benzylsulfones on normal fibroblasts and on tumor cells may be demonstrated by the assay described by Latham et al., Oncogene 12:827–837 (1996). Normal diploid lung human fibroblasts (HFL-1) or tumor cells (e.g., prostate, colo-rectal, breast, glial, pancreatic ovarian or leukemic) are plated in 6-well dishes at a cell density of $1.0 \times 10^5$ cells per 35-mm$^2$ well. The plated cells are treated 24 hours later with various concentrations of styrylbenzyl-sulfone dissolved in dimethyl sulfoxide (DMSO). The total number of viable cells is determined 96 hours later by trypsinizing the wells and counting the number of viable cells, as determined by trypan blue exclusion, using a hemacytometer. Normal HFL are treated with the same compounds under the same conditions of concentration and time.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound of the formula:

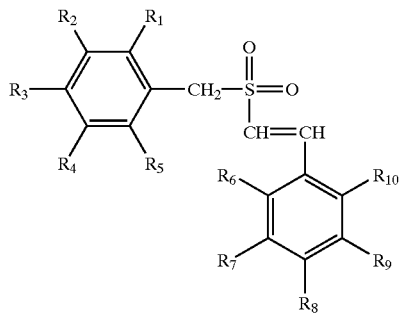

wherein (a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or (b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl;

or a pharmaceutically acceptable salt thereof.

2. A compound according to claim 1 having an E-configuration.

3. A compound according to claim 2 wherein
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

4. A compound according to claim 3 wherein $R_1$, $R_2$, $R_3$, $R_4$ and $R_5$ are halogen, same or different, and $R_6$, $R_7$, $R_8$, $R_9$ and $R_{10}$ are independently selected from the group consisting of hydrogen, halogen, C1–C3 alkyl and C1–C3 alkoxy.

5. A compound according to claim 4 wherein $R_8$ is halogen or C1–C3 alkoxy.

6. The compound according to claim 5 which is (E)-4-fluorostyryl-2,3,4,5,6-pentafluorobenzylsulfone.

7. The compound according to claim 5 which is (E)-4-chlorostyryl-2,3,4,5,6-pentafluorobenzylsulfone.

8. The compound according to claim 5 which is (E)-4-bromostyryl-2,3,4,5,6-pentafluorobenzylsulfone.

9. The compound according to claim 5 which is (E)-2,3,4,5,6-pentafluorostyryl-2,3,4,5,6-pentafluorobenzylsulfone.

10. A compound according to claim 3 wherein $R_3$ is C1–C6 alkoxy, at least two of $R_1$, $R_2$, $R_4$ and $R_5$ are C1–C6 alkoxy, and the remainder of $R_1$, $R_2$, $R_4$ and $R_5$ are hydrogen.

11. A compound according to claim 2 wherein:
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl.

12. The compound according to claim 11 which is (E)-2,3,4-trifluorostyryl-4-fluorobenzylsulfone.

13. The compound according to claim 11 which is (E)-2,3,4-trifluorostyryl-4-chlorobenzylsulfone.

14. A compound according to claim 11 wherein $R_6$, $R_7$, $R_8$, $R_9$ and $R_{10}$ are halogen, same or different, and $R_1$, $R_2$, $R_3$, $R_4$ and $R_5$ are independently selected from the group consisting of hydrogen, halogen, C1–C6 alkyl and C1–C6 alkoxy.

15. A compound according to claim 14 wherein $R_3$ is halogen or C1–C3 alkoxy.

16. The compound according to claim 15 which is (E)-2,3,4,5,6-pentafluorostyryl-4-fluorobenzylsulfone.

17. The compound according to claim 15 which is (E)-2,3,4,5,6-pentafluorostyryl-4-chlorobenzylsulfone.

18. The compound according to claim 15 which is (E)-2,3,4,5,6-pentafluorostyryl-4-bromobenzylsulfone.

19. The compound according to claim 15 which is (E)-2,3,4,5,6-pentafluorostyryl-3,4-dichlorobenzylsulfone.

20. The compound according to claim 15 which is (E)-2,3,4,5,6-pentafluorostyryl-4-iodobenzylsulfone.

21. A compound according to claim 11 wherein $R_3$ is selected from the group consisting of halogen, nitro, cyano, C1–C6 alkyl, C1–C6 alkoxy, hydroxyl, phosphonato, amino, sulfamyl, acetoxy, dimethylamino(C2–C6 alkoxy) and trifluoromethyl; and $R_1$, $R_2$, $R_4$ and $R_5$ are hydrogen; or a pharmaceutically acceptable salt thereof.

22. A compound according to claim 21 wherein the compound is (E)-3,4-dimethoxy-6-nitrostyryl-4-methoxybenzylsulfone.

23. A compound according to claim 21 of the formula:

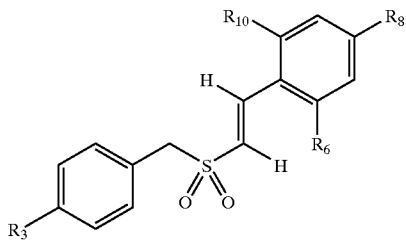

IV wherein:

$R_3$ and $R_8$ are independently selected from the group consisting of halogen, C1–C6 alkoxy, nitro, cyano, hydroxyl, phosphonato, amino, sulfamyl, acetoxy, dimethylamino(C2–C6 alkoxy) and trifluoromethyl; and $R_6$ and $R_{10}$ are independently selected from the group consisting of C1–C6 alkoxy, hydroxyl, phosphonato, amino, sulfamyl, acetoxy and dimethylamino(C2–C6 alkoxy).

24. The compound according to claim 23 wherein the compound is (E)-2-hydroxy-4,6-dimethoxystyryl-4-methoxybenzylsulfone, or a pharmaceutically acceptable salt thereof.

25. The compound according to claim 23 wherein the compound is (E)-2-hydroxy-4,6-dimethoxystyryl-4-chlorobenzylsulfone, or a pharmaceutically acceptable salt thereof.

26. A compound according to claim 23 wherein $R_6$ and $R_{10}$ are C1–C6 alkoxy.

27. The compound according to claim 26 which is (E)-2,6-dimethoxy-4-hydroxystyryl-4-methoxybenzylsulfone, or a pharmaceutically acceptable salt thereof.

28. A compound according to claim 23, wherein $R_3$ and $R_8$ are independently selected from the group consisting of halogen and C1–C6 alkoxy.

29. The compound according to claim 28 wherein the compound is (E)-2,6-dimethoxy-4-fluorostyryl-4-methoxybenzylsulfone.

30. The compound according to claim 28 wherein the compound is (E)-2,4,6-trimethoxystyryl-4-chlorobenzylsulfone.

31. The compound according to claim 28 wherein the compound is (E)-2,6-dimethoxy-4-fluorostyryl-4-chlorobenzylsulfone.

32. The compound according to claim 28 wherein the compound is (E)-2,4,6-trimethoxystyryl-4-bromobenzylsulfone.

33. The compound according to claim 28 wherein the compound is (E)-2,6-dimethoxy-4-fluorostyryl-4-bromobenzylsulfone.

34. A. compound according to claim 28 wherein $R_3$ and $R_8$ are C1–C6 alkoxy, same or different.

35. The compound according to claim 34 wherein the compound is (E)-2,4,6-trimethoxystyryl-4-methoxybenzylsulfone.

36. A compound according to claim 11 wherein $R_3$ is a halogen, $R_1$, $R_2$, $R_4$ and $R_5$ are hydrogen, and $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl and trifluoromethyl.

37. A compound according to claim 36 wherein $R_6$, $R_7$, $R_8$, $R_9$, and $R_{10}$ are selected from the group consisting of hydrogen, halogen and C1–C6 alkoxy.

38. A compound according to claim 37 wherein at least two of $R_6$, $R_7$, $R_8$, $R_9$ and $R_{10}$ are selected from C1–C6 alkoxy.

39. A compound according to claim 38 wherein the C1–C6 alkoxy groups are methoxy groups.

40. A compound according to claim 1 having a Z-configuration.

41. A compound according to claim 40 wherein:
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

42. A compound according to claim 41 wherein $R_1$, $R_2$, $R_3$, $R_4$ and $R_5$ are halogen and $R_6$, $R_7$, $R_8$, $R_9$ and $R_{10}$ are independently selected from the group consisting of hydrogen, halogen, C1–C3 alkyl and C1–C3 alkoxy.

43. A compound according to claim 41 wherein two of $R_1$, $R_2$, $R_3$, $R_4$ and $R_5$ are hydrogen and three of $R_1$, $R_2$, $R_3$, $R_4$ and $R_5$ are C1–C6 alkoxy.

44. A compound according to claim 43 wherein $R_6$, $R_7$, $R_8$, $R_9$ and $R_{10}$ are halogen.

45. A compound according to claim 40 wherein:
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, R, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy), and trifluoromethyl.

46. A compound according to claim 45 wherein $R_6$, $R_7$, $R_8$, $R_9$ and $R_{10}$ are halogen, same or different.

47. A compound according to claim 46 wherein $R_1$, $R_2$, $R_3$, $R_4$ and $R_5$ are independently selected from the group consisting of hydrogen, halogen, C1–C6 alkyl and C1–C6 alkoxy.

48. A compound according to claim 47 wherein two of $R_1$, $R_2$, $R_3$, $R_4$ and $R_5$ are hydrogen and three of $R_1$, $R_2$, $R_3$, $R_4$ and $R_5$ are C1–C6 alkoxy.

49. A compound according to claim 47 wherein $R_1$, $R_2$, $R_4$ and $R_5$ are hydrogen, and $R_3$ is other than hydrogen.

50. A compound according to claim 49 wherein $R_3$ is C1–C6 alkoxy or halogen.

51. A pharmaceutical composition comprising a pharmaceutically acceptable carrier and a compound according to claim 1.

52. A method of inducing apoptosis of tumor cells in an individual afflicted with cancer comprising administering to the individual an effective amount of a compound according to claim 1, or a pharmaceutically acceptable salt thereof, wherein the tumor cells are selected from the group consisting of ovarian, breast, prostate, lung, renal, colorectal and brain tumor cells.

53. A process for preparing a compound of claim 2 comprising condensing a compound of formula III

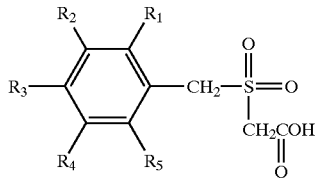

with a compound of formula VI:

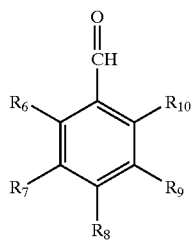

wherein
(a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or
(b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and (ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

54. A process according to claim 53 wherein the formula III compound is prepared by reacting sodium glycollate with a compound of the formula:

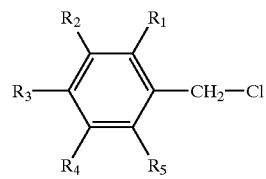

to form a benzylthioacetic acid compound of the formula

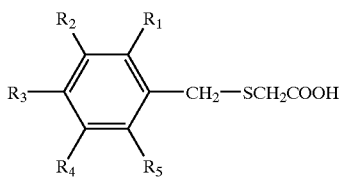

which is then oxidized to form said compound of formula III.

55. A process according to claim 54 wherein the benzylthioacetic acid compound is prepared by reacting a compound of the formula $HSCH_2COOR$ where R is C1–C6 alkyl with a compound of the formula:

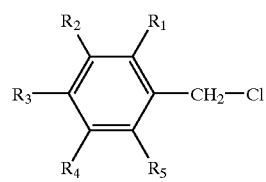

to form a compound of the formula II

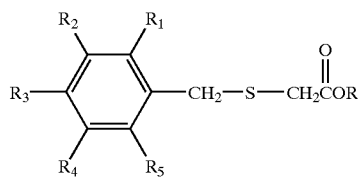

wherein

R is C1–C6alkyl;

and hydrolyzing the formula II compound to obtain said benzylthioacetic acid compound.

56. A process for preparing a compound according to claim 40 comprising reacting a compound of the formula:

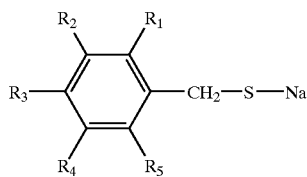

with a compound of the formula:

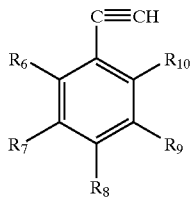

to form a Z configuration compound of formula IIa

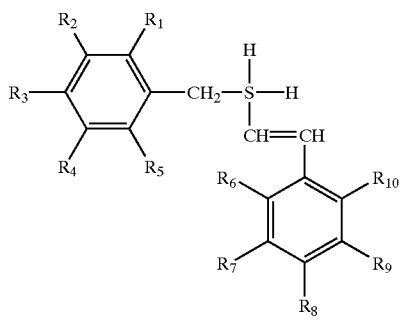

and oxidizing said formula IIa compound to form a compound according to claim 40;
wherein
(a)
(i) at least three of $R_1$, $R_2$, $R_3$, $R_4$ and $R_5$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; or (b)
(i) at least three of $R_6$, $R_7$, $R_8$, $R_9$ and $R_{10}$ are independently selected from the group consisting of halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl, and the balance of said $R_6$, $R_7$, $R_8$, $R_9$ and $R_{10}$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl; and
(ii) $R_1$, $R_2$, $R_3$, $R_4$ and $R_5$ are independently selected from the group consisting of hydrogen, halogen, C1–C6 alkyl, C1–C6 alkoxy, nitro, cyano, carboxyl, hydroxyl, phosphonato, amino, sulfamyl, acetoxy, dimethylamino(C2–C6 alkoxy) and trifluoromethyl.

57. An isolated optical isomer of a compound according to claim 1.

58. A pharmaceutical composition comprising a pharmaceutically acceptable carrier and a compound according to claim 2, or a pharmaceutically acceptable salt thereof.

59. A pharmaceutical composition comprising a pharmaceutically acceptable carrier and a compound according to claim 3.

60. A pharmaceutical composition comprising a pharmaceutically acceptable carrier and a compound according to claim 4.

61. A pharmaceutical composition comprising a pharmaceutically acceptable carrier and a compound according to claim 5.

62. A pharmaceutical composition comprising a pharmaceutically acceptable carrier and a compound according to claim 10.

63. A pharmaceutical composition comprising a pharmaceutically acceptable carrier and a compound according to claim 11.

64. A pharmaceutical composition comprising a pharmaceutically acceptable carrier and a compound according to claim 14.

65. A pharmaceutical composition comprising a pharmaceutically acceptable carrier and a compound according to claim 21.

66. A pharmaceutical composition comprising a pharmaceutically acceptable carrier and a compound according to claim 23.

67. A pharmaceutical composition comprising a pharmaceutically acceptable carrier and a compound according to claim 24.

68. A pharmaceutical composition comprising a pharmaceutically acceptable carrier and a compound according to claim 25.

69. A pharmaceutical composition comprising a pharmaceutically acceptable carrier and a compound according to claim 26.

70. A pharmaceutical composition comprising a pharmaceutically acceptable carrier and a compound according to claim 27.

71. A pharmaceutical composition comprising a pharmaceutically acceptable carrier and a compound according to claim 28.

72. A pharmaceutical composition comprising a pharmaceutically acceptable carrier and a compound according to claim 29.

73. A pharmaceutical composition comprising a pharmaceutically acceptable carrier and a compound according to claim 30.

74. A pharmaceutical composition comprising a pharmaceutically acceptable carrier and a compound according to claim 31.

75. A pharmaceutical composition comprising a pharmaceutically acceptable carrier and a compound according to claim 32.

76. A pharmaceutical composition comprising a pharmaceutically acceptable carrier and a compound according to claim 33.

77. A pharmaceutical composition comprising a pharmaceutically acceptable carrier and a compound according to claim 34.

78. A pharmaceutical composition comprising a pharmaceutically acceptable carrier and a compound according to claim 35.

79. A pharmaceutical composition comprising a pharmaceutically acceptable carrier and a compound according to claim 36.

80. A pharmaceutical composition comprising a pharmaceutically acceptable carrier and a compound according to claim 37.

81. A pharmaceutical composition comprising a pharmaceutically acceptable carrier and a compound according to claim 38.

82. A pharmaceutical composition comprising a pharmaceutically acceptable carrier and a compound according to claim 39.

83. A pharmaceutical composition comprising a pharmaceutically acceptable carrier and a compound according to claim 40.

84. A pharmaceutical composition comprising a pharmaceutically acceptable carrier and a compound according to claim 41.

85. A method of treating an individual for a cancer comprising administering to the individual an effective amount of a compound according to claim 1, or a pharmaceutically acceptable salt thereof, wherein the cancer is selected from the group consisting of ovarian, breast, prostate, lung, renal, colorectal, pancreatic and brain cancers, or the cancer is leukemia.

86. A method of treating an individual for a cancer comprising administering to the individual an effective amount of a compound according to claim 1, or a pharmaceutically acceptable salt thereof, wherein the cancer is selected from the group consisting of ovarian, breast, prostate, lung, renal, colorectal, pancreatic and brain cancers, or the cancer is leukemia.

* * * * *

UNITED STATES PATENT AND TRADEMARK OFFICE
CERTIFICATE OF CORRECTION

PATENT NO. : 6,486,210 B2
DATED : November 26, 2002
INVENTOR(S) : Reddy et al.

It is certified that error appears in the above-identified patent and that said Letters Patent is hereby corrected as shown below:

Column 29,
Line 20, cancel beginnning with "(i) at least three of" to and including "trifluoromethyl" in line 35, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;--

Column 29, line 59, to Column 30, line 7,
Cancel beginnning with "(i) at least three of" to and including "trifluoromethyl" and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and ifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Column 31,
Lines 1-2, delete "; or a pharmaceutically acceptable salt thereof"

Column 32,
Line 14, cancel beginnning with "(i) at least three of" to and including "trifluoromethyl" in line 28, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

UNITED STATES PATENT AND TRADEMARK OFFICE
CERTIFICATE OF CORRECTION

PATENT NO. : 6,486,210 B2
DATED : November 26, 2002
INVENTOR(S) : Reddy et al.

It is certified that error appears in the above-identified patent and that said Letters Patent is hereby corrected as shown below:

Column 33,
Line 38, cancel beginnning with "(i) at least three of" to and including "trifluoromethyl" in line 53, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Column 35,
Line 41, cancel beginnning with "(i) at least three of" to and including "trifluoromethyl" in line 56, and insert the following:

--(i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;--

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,486,210 B2 | Page 1 of 2 |
| APPLICATION NO. | : 09/833287 | |
| DATED | : November 26, 2002 | |
| INVENTOR(S) | : Reddy et al. | |

It is certified that error appears in the above-identified patent and that said Letters Patent is hereby corrected as shown below:

IN THE SPECIFICICATION

Column 3, line 55: "$R_1I$" should read --$R_1$--
Column 9 line 6: "means" should read --is meant--
Column 12 line 61: "Pagets Disease" should read --Paget's disease--
Column 12 line 62-63: "Peronies and Duputren's fibrosis" should read --Peyronie's and Dupuytren's fibroses--
Column 18 line 37: delete the expression "salicyclic, salicyclic,"
Column 18 line 42: "algenic" should read --alginic--
Column 18 line 42: "salicyclic" should read --salicylic--
Column 18 line 49: "to deleterious" should read --not deleterious--
Column 19 line 6: "Pagets Disease" should read --Paget's disease--
Column 19 line 7-8: "Peronies and Duputren's fibrosis" should read --Peyronie's and Dupuytren's fibroses--
Column 19 lines 27-28: "to deleterious" should read --not deleterious--

UNITED STATES PATENT AND TRADEMARK OFFICE
CERTIFICATE OF CORRECTION

PATENT NO.       : 6,486,210 B2
APPLICATION NO.  : 09/833287
DATED            : November 26, 2002
INVENTOR(S)      : Reddy et al.

It is certified that error appears in the above-identified patent and that said Letters Patent is hereby corrected as shown below:

IN THE CLAIMS

Column 35: replace the formula which follows line 21 with the following formula:

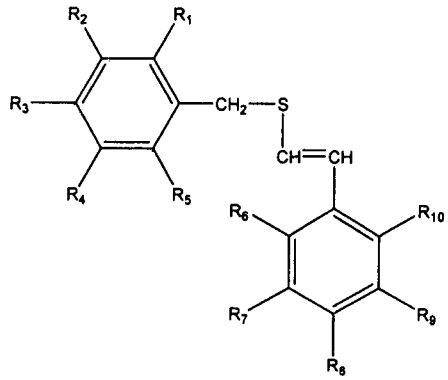

Column 35 line 37: "formula IIa" should read --formula Ia--

Signed and Sealed this

Twenty-fourth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,486,210 B2
APPLICATION NO. : 09/833287
DATED : November 26, 2002
INVENTOR(S) : Reddy et al.

It is certified that error appears in the above-identified patent and that said Letters Patent is hereby corrected as shown below:

IN THE CLAIMS

Column 29, line 20 claim 1, cancel beginning with "(i) at least three of" to and including "trifluoromethyl" in line 35, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Column 29, line 59 claim 3, cancel beginning with "(i) at least three of" to and including "trifluoromethyl" in column 30, line 7, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Column 31, line 1-2 claim 21, delete "; or a pharmaceutically acceptable salt thereof"

UNITED STATES PATENT AND TRADEMARK OFFICE
CERTIFICATE OF CORRECTION

PATENT NO.        : 6,486,210 B2
APPLICATION NO.   : 09/833287
DATED             : November 26, 2002
INVENTOR(S)       : Reddy et al.

It is certified that error appears in the above-identified patent and that said Letters Patent is hereby corrected as shown below:

Column 32, line 14 claim 41, cancel beginning with "(i) at least three of" to and including "trifluoromethyl" in line 28, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
      (ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
      (iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Column 33, line 38 claim 53, cancel beginning with "(i) at least three of" to and including "trifluoromethyl" in line 53, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
      (ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
      (iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

UNITED STATES PATENT AND TRADEMARK OFFICE
CERTIFICATE OF CORRECTION

PATENT NO. : 6,486,210 B2
APPLICATION NO. : 09/833287
DATED : November 26, 2002
INVENTOR(S) : Reddy et al.

It is certified that error appears in the above-identified patent and that said Letters Patent is hereby corrected as shown below:

Column 35, line 41 claim 56, cancel beginning with "(i) at least three of" to and including "trifluoromethyl" in line 56, and insert the following:

-- (i) $R_1$, $R_2$, $R_4$ and $R_5$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl;
(ii) $R_3$ is selected from the group consisting of hydrogen, halogen, C1-C6 alkyl, C1-C6 alkoxy, cyano, carboxyl, hydroxyl, phosphonato, amino, sulfamyl, acetoxy, dimethylamino(C2-C6 alkoxy) and trifluoromethyl, provided at least three of $R_1$, $R_2$, $R_3$, $R_4$ and $R_5$ are other than hydrogen; and
(iii) $R_6$, $R_7$, $R_8$, $R_9$ and $R_{10}$ are independently selected from the group consisting of hydrogen, halogen, C1-C6 alkyl, C1-C6 alkoxy, nitro, cyano, carboxyl, hydroxyl, phosphonato, amino, sulfamyl, acetoxy, dimethylamino(C2-C6 alkoxy) and trifluoromethyl; --

Signed and Sealed this

Third Day of June, 2008

JON W. DUDAS
*Director of the United States Patent and Trademark Office*